(12) United States Patent
Oki et al.

(10) Patent No.: US 12,024,618 B2
(45) Date of Patent: Jul. 2, 2024

(54) RESIN PARTICLES

(71) Applicant: FUJIFILM Business Innovation Corp., Tokyo (JP)

(72) Inventors: Masahiro Oki, Kanagawa (JP); Kenji Yao, Kanagawa (JP); Hideaki Yoshikawa, Kanagawa (JP); Kazusei Yoshida, Kanagawa (JP); Tetsuya Taguchi, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 0 days.

(21) Appl. No.: 17/504,524

(22) Filed: Oct. 19, 2021

(65) Prior Publication Data
US 2022/0306842 A1    Sep. 29, 2022

(30) Foreign Application Priority Data
Mar. 25, 2021 (JP) .................... 2021-052446

(51) Int. Cl.
*C08L 1/14* (2006.01)
*A61K 8/73* (2006.01)
*C08L 1/12* (2006.01)

(52) U.S. Cl.
CPC .............. *C08L 1/14* (2013.01); *A61K 8/731* (2013.01); *C08L 1/12* (2013.01); *C08L 2201/06* (2013.01)

(58) Field of Classification Search
CPC .......... C08L 1/12; C08L 1/14; C08L 2201/06; A61K 8/731
USPC ......................................................... 524/39
See application file for complete search history.

(56) References Cited

U.S. PATENT DOCUMENTS

| | | | |
|---|---|---|---|
| 6,120,802 A | 9/2000 | Breitenbach et al. | |
| 9,949,897 B2 | 4/2018 | Shiroya et al. | |
| 10,064,806 B2 | 9/2018 | Lee | |
| 2010/0310667 A1 | 12/2010 | Castan et al. | |
| 2014/0113826 A1* | 4/2014 | Fallon | A61Q 19/00 424/405 |
| 2017/0216498 A1 | 8/2017 | Kang et al. | |
| 2018/0235849 A1 | 8/2018 | Shiroya et al. | |
| 2018/0265805 A1 | 9/2018 | Gerke et al. | |

FOREIGN PATENT DOCUMENTS

| | | | | |
|---|---|---|---|---|
| CN | 107141950 | 10/2018 | | |
| EP | 0575143 | 8/1997 | | |
| EP | 0857062 | 4/2002 | | |
| EP | 3932974 | 1/2022 | | |
| JP | 2004256579 | 9/2004 | | |
| JP | 2015512863 | 4/2015 | | |
| KR | 20190095764 A * | 2/2020 | ................ | C08J 5/18 |
| WO | WO-2012038061 A2 * | 3/2012 | ............. | A61K 47/44 |
| WO | 2017045893 | 3/2017 | | |

OTHER PUBLICATIONS

English Machine Translation KR20190095764 (A) Obtained at 20190095764-Claims-en (epo.org) (Year: 2019).*
"Search Report of Europe Counterpart Application", issued on May 23, 2022, p. 1-p. 8.
"Office Action of Europe Counterpart Application", issued on Nov. 25, 2022, with English translation thereof, pp. 1-5.
"Office Action of Europe Counterpart Application", issued on May 10, 2023, p. 1-p. 6.
Zeus, "Friction and Wear of Polymers", Jan. 2005, pp. 1-9. Available at http://www.appstate.edu/~clementsjs/polymerproperties/$p$lastics_$f$riction$5f$w$ear.pdf.
"Office Action of Europe Counterpart Application", issued on Sep. 22, 2023, pp. 1-6.
"Office Action of Europe Counterpart Application", issued on Jan. 19, 2024, p. 1-p. 6.

* cited by examiner

*Primary Examiner* — Ling Siu Cho
*Assistant Examiner* — Ronald Grinsted
(74) *Attorney, Agent, or Firm* — JCIPRNET

(57) ABSTRACT

Resin particles include mother particles containing a biodegradable resin, and a coating layer containing at least one selected from the group consisting of a quaternary ammonium salt-containing polymer, polyacrylamide, polyvinylpyrrolidone, and polylysine on a surface of the mother particles.

6 Claims, No Drawings

RESIN PARTICLES

CROSS-REFERENCE TO RELATED APPLICATIONS

This application is based on and claims priority under 35 USC 119 from Japanese Patent Application No. 2021-052446 filed Mar. 25, 2021.

BACKGROUND

(i) Technical Field

The present invention relates to resin particles.

(ii) Related Art

JP2004-256579A suggests "a cellulose material having improved biodegradability by coating with a water-soluble polymer".

JP2015-512863A suggests "a cosmetic method for changing appearance of a skin, changing feel of the skin, and/or protecting the skin, the cosmetic method including a step of applying a self-supporting beauty sheet containing at least one biocompatible and/or biodegradable hydrophobic polymer layer on the skin, in which the self-supporting beauty sheet, for example, has a thickness of 10 to 1,000 nm, preferably 30 to 500 nm, and more preferably 50 to 300 nm".

SUMMARY

Aspects of non-limiting embodiments of the present disclosure relate to resin particles having mother particles containing a biodegradable resin, the resin particles having high fluidity compared to a case where a surface of the mother particle is not modified, or a case where a dynamic friction coefficient exceeds 0.5.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

The object is addressed by the following means.

According to an aspect of the present disclosure, there are provided resin particles including mother particles containing a biodegradable resin, and a coating layer containing at least one selected from the group consisting of a quaternary ammonium salt-containing polymer, polyacrylamide, polyvinylpyrrolidone, and polylysine on a surface of the mother particles.

DETAILED DESCRIPTION

Hereinafter, exemplary embodiments of the present invention will be described. These descriptions and examples illustrate embodiments and do not limit the scope of the invention.

In the numerical value range described stepwise in the present specification, an upper limit value or a lower limit value described in one numerical value range may be substituted with an upper limit value or a lower limit value of another numerical value range described stepwise. In addition, in the numerical value range described in the present specification, the upper limit value or the lower limit value of the numerical value range may be substituted with the value shown in the examples.

Each component may contain a plurality of substances. In a case of referring to an amount of each component in a composition, in a case where the plurality of substances corresponding to each component is present in the composition, unless otherwise specified, the amount means a sum of the plurality of substances present in the composition.

In the present specification, (meth)acrylic means both acrylic and methacrylic.

In the present specification, the term of "step" is included in the present term as long as an intended purpose of the step is achieved not only as an independent step but also in a case where the step is not clearly distinguished from other steps.

Resin Particles

The resin particles according to a first embodiment include mother particles containing a biodegradable resin and a coating layer containing at least one selected from the group consisting of a quaternary ammonium salt-containing polymer, polyacrylamide, polyvinylpyrrolidone, and polylysine on a surface of the mother particles.

Due to the configuration, the fluidity of the resin particles according to the first embodiment is improved. The reason is presumed as follows.

The resin particles containing a biodegradable resin (hereinafter, also referred to as biodegradable resin particles) may not have sufficient fluidity of the particles. Therefore, for example, in a case where biodegradable resin particles are used for cosmetic use and resin filler use, the particles may cause aggregation and the like.

The resin particles according to a first embodiment include mother particles containing a biodegradable resin and a coating layer containing at least one selected from the group consisting of a quaternary ammonium salt-containing polymer, polyacrylamide, polyvinylpyrrolidone, and polylysine on a surface of the mother particles. By having the coating layer, slipperiness of the resin particle surface is easily improved. Therefore, the friction between the resin particles easily decreases, and the fluidity of the particles is easily improved.

From the above, it is presumed that the fluidity of the resin particles according to the first embodiment is improved.

The resin particles according to a second embodiment include mother particles containing a biodegradable resin and a coating layer on a surface of the mother particles, and a dynamic friction coefficient is 0.5 or less.

Due to the configuration, the fluidity of the resin particles according to the second embodiment is improved. The reason is presumed as follows.

The resin particles according to the second embodiment have a coating layer on the surface of the mother particles, and a dynamic friction coefficient is 0.5 or less. By setting the dynamic friction coefficient of the resin particles within the numerical value range, the friction between the resin particles easily decreases, and the fluidity of the particles is easily improved.

From the above, it is presumed that the fluidity of the resin particles according to the second embodiment is improved.

Hereinafter, the resin particles corresponding to any one of the resin particles according to the first or second embodiment will be described in detail. However, an example of the resin particles of the present invention may be resin particles corresponding to any one of the resin particles according to the first or second embodiment.

Mother Particles

Biodegradable Resin

Mother particles contain a biodegradable resin.

Examples of the mother particles include particles containing a biodegradable resin as a major component, and specific examples thereof include 90% by mass, 95% by mass, 98% by mass, or 100% by mass of the biodegradable resin with respect to the total amount of the mother particles.

Here, the biodegradable resin is a resin that is decomposed into water and carbon dioxide by microorganisms. Specifically, the biodegradable resin means a resin in which the biodegradation rate under aerobic conditions measured by a method in accordance with ISO-14855-2 (2018) is 50% or more in one month.

Examples of the biodegradable resin include cellulose acylate, polyester, natural polymers, and the like.

Cellulose acylate is a cellulose derivative in which at least a part of hydroxy groups in cellulose is substituted (acylated) with an acyl group. The acyl group is a group having a structure of $-CO-R^{AC}$ ($R^{AC}$ represents a hydrogen atom or a hydrocarbon group). Examples of the cellulose acylate include a cellulose derivative represented by General Formula (CA).

Examples of the polyester include an aliphatic polyester, an aliphatic aromatic polyester, and the like.

Examples of the aliphatic polyester include polyhydroxyalkanoic acid such as polylactic acid (PLA), polyglycolic acid (PGA) polyhydroxybutyrate, poly (3-hydroxybutyrate-co-3-hydroxyhexanoate) (PHBH), polycaprolactone, polybutylene succinate (PBS), polybutylene succinate/adipate (PBSA), and polyethylene succinate (PBA); and the like.

Examples of the aliphatic aromatic polyester include polybutylene adipate/terephthalate copolymer resin (PBAH), polytetramethylene adipate/terephthalate copolymer resin, and the like.

Examples of natural polymers include starch, cellulose, chitin, chitosan, gluten, gelatin, zein, soybean protein, collagen, keratin, and the like.

The biodegradable resin is, for example, preferably at least one selected from the group consisting of cellulose acylate and polyester, and more preferably cellulose acylate.

By containing the compound as a biodegradable resin, it becomes easy to react with the compound contained in the coating layer. Therefore, in a case of forming the coating layer, the coating layer easily becomes a more uniform skin coating layer. Therefore, the fluidity of the resin particles is further improved.

In addition, the resin particles containing cellulose acylate as a biodegradable resin have a tendency to decrease the fluidity of the particles. However, for the above reason, even in a case where the resin particles according to the present exemplary embodiment contain cellulose acylate as a biodegradable resin, the fluidity of the resin particles is improved.

Cellulose Acylate

Cellulose acylate is, for example, a cellulose derivative represented by General Formula (CA).

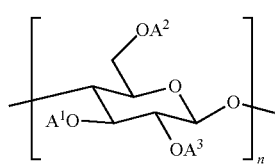

General Formula (CA)

In General Formula (CA), A1, A2, and A3 each independently represent a hydrogen atom or an acyl group, and n represents an integer of 2 or more. However, at least a part of n A1s, n A2s, or n A3s represents an acyl group. The n A1s in a molecule may be all the same, partially the same, or different from each other. Similarly, the n A2s and n A3s in the molecule may be all the same, partially the same, or different from each other.

In the acyl group represented by A1, A2, and A3, a hydrocarbon group in the acyl group may be linear, branched, or cyclic, but the acyl group is, for example, preferably linear or branched, and more preferably linear.

In the acyl group represented by A1, A2, and A3, a hydrocarbon group in the acyl group may be a saturated hydrocarbon group, or an unsaturated hydrocarbon group, but the acyl group is, for example, preferably a saturated hydrocarbon group.

The acyl group represented by A1, A2, and A3 is, for example, preferably an acyl group having 1 to 6 carbon atoms. That is, the cellulose acylate is, for example, preferably a cellulose acylate containing an acyl group having 1 or more and 6 or less carbon atoms.

The acyl group represented by A1, A2, and A3 may be a group in which a hydrogen atom in the acyl group is substituted with a halogen atom (for example, a fluorine atom, a bromine atom, an iodine atom), an oxygen atom, a nitrogen atom, and the like but is, for example, preferably not substituted.

Examples of the acyl group represented by A1, A2, and A3 include a formyl group, an acetyl group, a propionyl group, a butyryl group (butanoyl group), a propenoyl group, a hexanoyl group, and the like. Among these, the acyl group is, for example, preferably an acyl group having two or more and four or less carbon atoms, and more preferably an acyl group having two or three carbon atoms, from a viewpoint of improving the biodegradation rate of the resin particles.

Examples of the cellulose acylate include cellulose acetate (cellulose monoacetate, cellulose diacetate (DAC), cellulose triacetate), cellulose acetate propionate (CAP), cellulose acetate butyrate (CAB), and the like.

Cellulose acylate is, for example, preferably, cellulose acylate having two or more acyl groups, from a viewpoint of improving the biodegradation rate of the resin particles. Specifically, the cellulose acylate is, for example, preferably cellulose acetate, cellulose acetate propionate (CAP), and cellulose acetate butyrate (CAB), and more preferably cellulose acetate propionate (CAP), from a viewpoint of improving the biodegradation rate of the resin particles.

By using at least one selected from cellulose acetate, cellulose acetate propionate (CAP), and cellulose acetate butyrate (CAB) as the cellulose acylate, it becomes easy to react with the compound contained in the coating layer. Therefore, in a case of forming the coating layer, the coating layer easily becomes a more uniform skin coating layer. Therefore, the fluidity of the resin particles is further improved.

One cellulose acylate may be used alone, or two or more thereof may be used in combination.

A weight average polymerization degree of cellulose acylate is, for example, preferably 200 or more and 1,000 or less, more preferably 500 or more and 1,000 or less, and further more preferably 600 or more and 1,000 or less.

The weight average polymerization degree of cellulose acylate is obtained from a weight average molecular weight (Mw) by the following procedure.

First, the weight average molecular weight (Mw) of cellulose acylate is measured by gel permeation chromatography (GPC apparatus: manufactured by Tosoh Corporation, HLC-8320GPC, column: TSKgel α-M) in terms of polystyrene using tetrahydrofuran.

Subsequently, the polymerization degree of cellulose acylate is obtained by dividing by a structural unit molecular weight of cellulose acylate. For example, in a case where a substituent of cellulose acylate is an acetyl group, the structural unit molecular weight is 263 in a case where a substitution degree is 2.4, and 284 in a case where the substitution degree is 2.9.

A substitution degree of cellulose acylate is, for example, preferably 2.1 or more and 2.9 or less, more preferably 2.2 or more and 2.9 or less, further more preferably 2.3 or more and 2.9 or less, and particularly preferably 2.6 or more and 2.9 or less, from a viewpoint of improving the biodegradation rate of the resin particles.

In cellulose acetate propionate (CAP), a ratio of the substitution degree of the acetyl group to the propionyl group (acetyl group/propionyl group) is, for example, preferably 0.01 or more and 1 or less, and more preferably 0.05 or more and 0.1 or less, from a viewpoint of improving the biodegradation rate of the resin particles.

In cellulose acetate butyrate (CAB), a ratio of the substitution degree of the acetyl group to the butyryl group (acetyl group/butyryl group) is, for example, preferably 0.05 or more and 3.5 or less, and more preferably 0.5 or more and 3.0 or less, from a viewpoint of improving the biodegradation rate of the resin particles.

The substitution degree of cellulose acylate is an index indicating a degree to which a hydroxy group of cellulose is substituted with an acyl group. That is, the substitution degree is an index indicating a degree of acylation of cellulose acylate. Specifically, the substitution degree means an intramolecular average number of substitutions in which three hydroxy groups in a D-glucopyranose unit of cellulose acylate are substituted with acyl groups. The substitution degree is obtained from an integral ratio of peaks of cellulose-derived hydrogen and acyl group-derived hydrogen in 1H-NMR (JMN-ECA/manufactured by JEOL RESONANCE Inc.).

One biodegradable resin may be used alone, or a plurality of thereof may be used in combination.

Plasticizer

The mother particles, for example, preferably contain a plasticizer.

The plasticizer tends to contain a functional group that easily reacts with the compound contained in the coating layer. Therefore, as the mother particles contain a plasticizer, the compound contained in the coating layer reacts not only with the biodegradable resin contained in the mother particles but also with the plasticizer. Therefore, in a case of forming the coating layer, the coating layer easily becomes a more uniform skin coating layer. Therefore, the fluidity of the resin particles is further improved.

Examples of the plasticizer include ester compound, cardanol compound, camphor, metal soap, polyol, polyalkylene oxide, and the like. The plasticizer is, for example, preferably at least one an ester compound or a cardanol compound. One plasticizer may be used alone, or two or more thereof may be used in combination.

By using at least one an ester compound or a cardanol compound as the plasticizer, the plasticizer easily reacts with the compound contained in the coating layer. Therefore, in a case of forming the coating layer, the coating layer easily becomes a more uniform skin coating layer. Therefore, the fluidity of the resin particles is further improved.

Examples of the ester compound include fatty acid ester (adipic acid ester, citric acid ester, sebacic acid ester, azelaic acid ester, phthalic acid ester, acetic acid ester), phosphoric acid ester, condensed phosphoric acid ester, glycol ester (for example, benzoic acid glycol ester), modified body of fatty acid ester (for example, epoxidized fatty acid ester), and the like. Examples of the ester include monoester, diester, triester, polyester, and the like. Among these, dicarboxylic acid diester (adipic acid diester, sebacic acid diester, azelaic acid diester, phthalic acid diester, and the like) is, for example, preferable.

The plasticizer is, for example, preferably at least one selected from the group consisting of adipic acid ester, citric acid ester, and sebacic acid ester. Adipic acid ester, citric acid ester, and sebacic acid ester have a high affinity for cellulose acylate, and are dispersed in a state close to uniform with respect to cellulose acylate, and thus easily react with the compound contained in the coating layer compared to other plasticizers.

As the adipic acid ester, a mixture of the adipic acid ester and components other than adipic acid ester may be used. Examples of commercially available products of the mixture include Daifatty101 manufactured by Daihachi Chemical Industry Co., Ltd., and the like.

Examples of fatty acid ester such as citric acid ester, sebacic acid ester, azelaic acid ester, phthalic acid ester, and acetic acid ester include esters of fatty acid and alcohol. Examples of the alcohol include monohydric alcohols such as methanol, ethanol, propanol, butanol, and 2-ethylhexanol; polyhydric alcohols such as glycerin, polyglycerin (diglycerin and the like), pentaerythritol, ethylene glycol, diethylene glycol, propylene glycol, butylene glycol, trimethylolpropane, trimethylolethane, and sugar alcohol; and the like.

Examples of the glycol in the benzoic acid glycol ester include ethylene glycol, diethylene glycol, propylene glycol, and the like.

The epoxidized fatty acid ester is an ester compound having a structure in which carbon-carbon unsaturated bond of the unsaturated fatty acid ester is epoxidized (that is, oxacyclopropane). Examples of the epoxidized fatty acid ester include esters of fatty acid and alcohol in which a part or all of the carbon-carbon unsaturated bonds in the unsaturated fatty acid (for example, oleic acid, palmitoleic acid, vaccenic acid, linoleic acid, linolenic acid, nervonic acid, and the like) is epoxidized. Examples of the alcohol include monohydric alcohols such as methanol, ethanol, propanol, butanol, and 2-ethylhexanol; polyhydric alcohols such as glycerin, polyglycerin (diglycerin and the like), pentaerythritol, ethylene glycol, diethylene glycol, propylene glycol, butylene glycol, trimethylolpropane, trimethylolethane, and sugar alcohol; and the like.

The ester compound as a plasticizer has a molecular weight (or weight average molecular weight) of, for example, preferably 200 or more and 2,000 or less, more preferably 250 or more and 1,500 or less, and further more preferably 280 or more and 1,000 or less. Unless otherwise specified, the weight average molecular weight of the ester compound is a value measured in accordance with a method for measuring the weight average molecular weight of cellulose acylate.

As the plasticizer, a cardanol compound is, for example, preferably used.

The cardanol compound refers to a component contained in a naturally-derived compound made from cashew (for example, a compound represented by Structural Formulae (b-1) to (b-4)) or a derivative from the component.

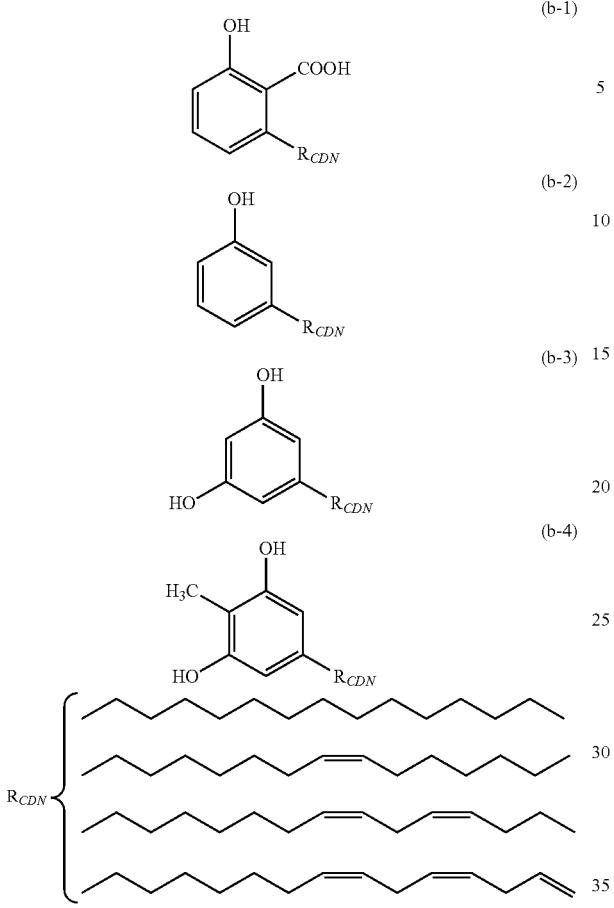

The cardanol compound may be a mixture of the naturally-derived compound made from cashew (hereinafter, also referred to as "cashew-derived mixture").

The cardanol compound may be a derivative from a cashew-derived mixture. Examples of the derivative from the cashew-derived mixture include the following mixtures or monomers, for example.

A mixture in which a composition ratio of each component in the cashew-derived mixture is adjusted A monomer obtained by isolating only specific components from a cashew-derived mixture A mixture that contains a modified body obtained by modifying the components in the cashew-derived mixture A mixture that contains a polymer obtained by polymerizing components in a cashew-derived mixture A mixture that contains a modified polymer obtained by modifying and polymerizing components in a cashew-derived mixture A mixture that contains a modified body obtained by further modifying components in the mixture having the adjusted composition ratio A mixture that contains a polymer obtained by further polymerizing the components in the mixture having the adjusted composition ratio A mixture that contains a modified polymer obtained by further modifying and polymerizing the components in the mixture having the adjusted composition ratio A modified body obtained by further modifying the isolated monomer A polymer obtained by further polymerizing the isolated monomer A modified polymer obtained by further modifying and polymerizing the isolated monomer Here, it is assumed that the monomer also includes multimers such as dimer and trimer.

The cardanol compound is, for example, preferably at least one compound selected from the group consisting of a compound represented by General Formula (CDN1) or a polymer obtained by polymerizing the compound represented by General Formula (CDN1), from a viewpoint of improving the biodegradation rate of the resin particles.

General Formula (CDN1)

In General Formula (CDN1), $R^1$ represents an alkyl group that may have a substituent or an unsaturated aliphatic group that has a double bond and may have a substituent. $R^2$ represents a hydroxy group, a carboxy group, an alkyl group that may have a substituent, or an unsaturated aliphatic group that has a double bond and may have a substituent. P2 represents an integer of 0 or more and 4 or less. $R^2$ present in plural numbers in a case where P2 is 2 or more may be the same groups or may be different groups.

In General Formula (CDN1), the alkyl group that may have a substituent represented by $R^1$ is, for example, preferably an alkyl group having 3 or more and 30 or less carbon atoms, more preferably an alkyl group having 5 or more and 25 or less carbon atoms, and further more preferably an alkyl group having 8 or more and 20 or less carbon atoms.

Examples of the substituent include a hydroxy group; a substituent containing an ether bond such as an epoxy group and a methoxy group; a substituent containing an ester bond such as an acetyl group and a propionyl group; and the like.

Examples of alkyl group that may have a substituent include a pentadecane-1-yl group, a heptane-1-yl group, an octane-1-yl group, a nonane-1-yl group, a decane-1-yl group, an undecane-1-yl group, a dodecane-1-yl group, a tetradecane-1-yl group, and the like.

In General Formula (CDN1), the unsaturated aliphatic group that has a double bond represented by $R^1$ and may have a substituent is, for example, preferably an unsaturated aliphatic group having 3 or more and 30 or less carbon atoms, more preferably an unsaturated aliphatic group having 5 or more and 25 or less carbon atoms, and further more preferably an unsaturated aliphatic group having 8 or more and 20 or less carbon atoms.

The number of double bonds included in the unsaturated aliphatic group is, for example, preferably 1 or more and 3 or less.

Examples of the substituent include the same as exemplified as the substituent of the alkyl group.

Examples of the unsaturated aliphatic group that has a double bond and may have a substituent include a pentadeca-8-ene-1-yl group, a pentadeca-8,11-diene-1-yl group, a pentadeca-8,11,14-triene-1-yl group, a pentadeca-7-ene-1-yl group, a pentadeca-7,10-diene-1-yl group, a pentadeca-7,10,14-triene-1-yl group, and the like.

In General Formula (CDN1), $R^1$ is, for example, preferably a pentadeca-8-ene-1-yl group, a pentadeca-8,11-diene-1-yl group, a pentadeca-8,11,14-triene-1-yl group, a pentadeca-7-ene-1-yl group, a pentadeca-7,10-diene-1-yl group, a pentadeca-7,10,14-triene-1-yl group, and the like.

In General Formula (CDN1), as an alkyl group that may have a substituent represented by $R^2$ and an unsaturated aliphatic group that has a double bond and may have a substituent, exemplified alkyl groups that may have a substituent represented by $R^1$ and unsaturated aliphatic groups that have a double bond and may have a substituent are similarly exemplified as, for example, preferable examples.

The compound represented by General Formula (CDN1) may be further modified. For example, the compound may be epoxidized, and from a viewpoint of improving the biodegradation rate of the resin particles, specifically, may be a compound of a structure in which a hydroxy group of the compound represented by General Formula (CDN1) has been substituted with the following group (EP), that is, a compound represented by General Formula (CDN1-e) is, for example, preferable.

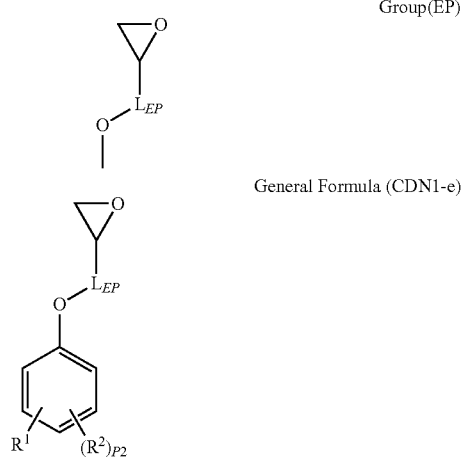

Group(EP)

General Formula (CDN1-e)

In the group (EP) and General Formula (CDN1-e), $L_{EP}$ represents a single bond or a divalent linking group. In General Formula (CDN1-e), $R^1$, $R^2$, and P2 each are the same as $R^1$, $R^2$, and P2 in General Formula (CDN1).

In the group (EP) and General Formula (CDN1-e), examples of the divalent linking group represented by $L_{EP}$ include an alkylene group that may have a substituent (for example, preferably an alkylene group having 1 or more and 4 or less carbon atoms), more preferably an alkylene group having 1 carbon atom), a —$CH_2CH_2OCH_2CH_2$— group, and the like.

Examples of the substituent include the same as exemplified as the substituent in $R^1$ of General Formula (CDN1).

The $L_{EP}$ is, for example, preferably a methylene group.

A polymer obtained by polymerizing the compound represented by General Formula (CDN1) refers to a polymer obtained by polymerizing at least two or more compounds represented by General Formula (CDN1) via or not via a linking group.

Examples of the polymer obtained by polymerizing the compound represented by General Formula (CDN1) include a compound represented by General Formula (CDN2).

General Formula (CDN2)

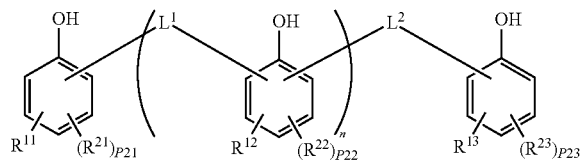

In General Formula (CDN2), $R^{11}$, $R^{12}$, and $R^{13}$ each independently represent an alkyl group that may have a substituent, or an unsaturated aliphatic group that has a double bond and may have a substituent. $R^{21}$, $R^{22}$, and $R^{23}$ each independently represent a hydroxy group, a carboxy group, an alkyl group that may have a substituent, or an unsaturated aliphatic group that has a double bond and may have a substituent. P21 and P23 each independently represent an integer of 0 or more and 3 or less, and P22 represents an integer of 0 or more and 2 or less. $L^1$ and $L^2$ each independently represent a divalent linking group. n represents an integer of 0 or more and 10 or less. $R^{21}$ present in plural numbers in a case where P21 is 2 or more, $R^{22}$ present in plural numbers in a case where P22 is 2 or more, and $R^{23}$ present in plural numbers in a case where P23 is 2 or more may be each independently the same groups, or may be different groups. $R^{12}$, $R^{22}$, and $L^1$ present in plural numbers in a case where n is 2 or more may be each independently the same groups, or may be different groups, and P22 present in plural numbers in a case where n is 2 or more may be the same numbers, or may be different numbers.

In General Formula (CDN2), as an alkyl group that may have a substituent represented by $R^{11}$, $R^{12}$, $R^{13}$, $R^{21}$, $R^{22}$, and $R^{23}$ and an unsaturated aliphatic group that has a double bond and may have a substituent, exemplified $R^1$ of General Formula (CDN1) is similarly exemplified as, for example, a preferable example.

In General Formula (CDN2), examples of the divalent linking group represented by $L^1$ and $L^2$ include an alkylene group that may have a substituent (for example, preferably an alkylene group having 2 or more and 30 or less carbon atoms, more preferably an alkylene group having 5 or more and 20 or less carbon atoms), and the like.

Examples of the substituent include the same as exemplified as the substituent in $R^1$ of General Formula (CDN1).

In General Formula (CDN2), n is, for example, preferably 1 or more and 10 or less, and more preferably 1 or more and 5 or less.

The compound represented by General Formula (CDN2) may be further modified. For example, the compound may be epoxidized, and specifically, may be a compound of a structure in which a hydroxy group of the compound represented by General Formula (CDN2) has been substituted with a group (EP), that is, a compound represented by General Formula (CDN2-e).

General Formula (CDN2-e)

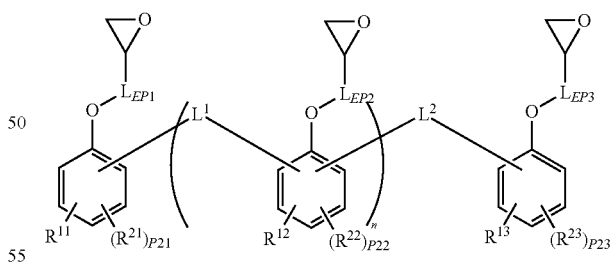

In General Formula (CDN2-e), $R^{11}$, $R^{12}$, $R^{13}$, $R^{21}$, $R^{22}$, $R^{23}$, P21, P22, P23, $L^1$, $L^2$, and n are each independently the same as $R^{11}$, $R^{12}$, $R^{13}$, $R^{21}$, $R^{22}$, $R^{23}$, $P^{21}$, $P^{22}$, $P^{23}$, $L^1$, $L^2$, and n in General Formula (CDN2).

In General Formula (CDN2-e), $L_{EP1}$, $L_{EP2}$, and $L_{EP3}$ each independently represent a single bond or a divalent linking group. $L_{EP2}$ present in plural numbers in a case where n is 2 or more may be the same groups, or may be different groups.

In General Formula (CDN2-e), as the divalent linking group represented by $L_{EP1}$, $L_{EP2}$, and $L_{EP3}$, exemplified divalent linking groups represented by $L_{EP}$ in General Formula (CDN1-e) are similarly exemplified as, for example, preferable examples.

The polymer obtained by polymerizing the compound represented by General Formula (CDN1) may be, for example, a polymer obtained by three-dimensionally cross-linking and polymerizing at least three or more compounds represented by General Formula (CDN1) via or not via a linking group. Examples of the polymer obtained by three-dimensionally cross-linking and polymerizing the compound represented by General Formula (CDN1) include a compound represented by the following structural formula, for example.

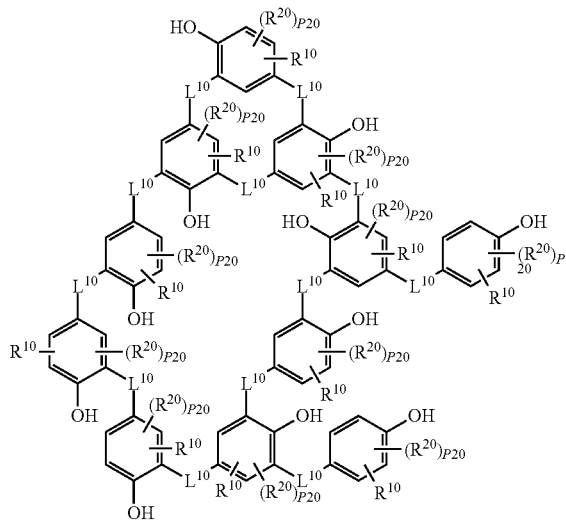

In the structural formula, $R^{10}$, $R^{20}$, and P20 each are the same as $R^1$, $R^2$, and P2 in General Formula (CDN1). $L^{10}$ represents a single bond or a divalent linking group. $R^{10}$, $R^{20}$, and $L^{10}$ present in plural numbers each may be the same groups, or may be different groups. P20 present in plural numbers may be the same numbers, or may be different numbers.

In the structural formula, the divalent linking group represented by $L^{10}$ includes an alkylene group that may have a substituent (for example, preferably an alkylene group having 2 or more and 30 or less carbon atoms, more preferably 5 or more and 20 or less carbon atoms), and the like.

Examples of the substituent include the same as exemplified as the substituent in $R^1$ of General Formula (CDN1).

The compound represented by the structural formula may be further modified, for example, may be epoxidized. Specifically, the compound may be a compound of a structure in which the hydroxy group of the compound represented by the structural formula is substituted with a group (EP), for example, a compound represented by the following structural formula, that is, a polymer obtained by three-dimensionally cross-linking and polymerizing the compound represented by General Formula (CDN1-e).

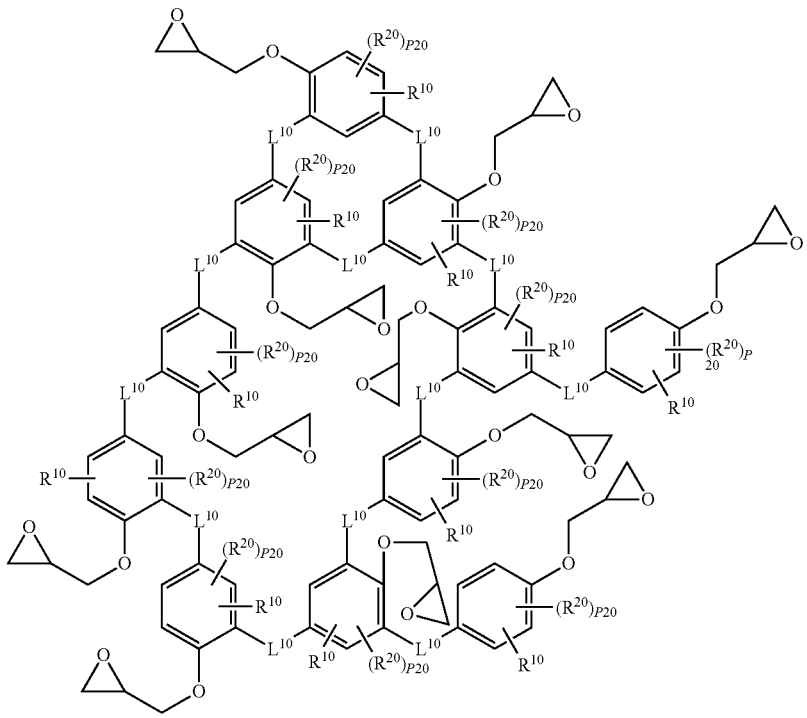

In the structural formula, $R^{10}$, $R^{20}$, and P20 are each independently the same as $R^1$, $R^2$, and P2 in General Formula (CDN1-e). $L^{10}$ represents a single bond or a divalent linking group. $R^{10}$, $R^{20}$, and $L^{10}$ present in plural numbers each may be the same groups, or may be different groups. P20 present in plural numbers may be the same numbers, or may be different numbers.

In the structural formula, the divalent linking group represented by $L^{10}$ includes an alkylene group that may have a substituent (for example, preferably an alkylene group having 2 or more and 30 or less carbon atoms, more preferably 5 or more and 20 or less carbon atoms), and the like.

Examples of the substituent include the same as exemplified as the substituent in $R^1$ of General Formula (CDN1).

The cardanol compound, for example, preferably include a cardanol compound having an epoxy group, and is, for example, more preferably a cardanol compound having an epoxy group, from a viewpoint of improving the transparency of a resin molded body.

As the cardanol compound, a commercially available product may be used. Examples of the commercially available product include NX-2024, Ultra LITE 2023, NX-2026, GX-2503, NC-510, LITE 2020, NX-9001, NX-9004, NX-9007, NX-9008, NX-9201, and NX-9203, manufactured by Cardolite Corporation, LB-7000, LB-7250, and CD-5L, manufactured by Tohoku Chemical Industries, Ltd., and the like. Examples of the commercially available product of the cardanol compound having an epoxy group include NC-513, NC-514S, NC-547, LITE 513E, and Ultra LTE 513, manufactured by Cardolite Corporation, and the like.

A hydroxyl value of the cardanol compound is, for example, preferably 100 mgKOH/g or more, more preferably 120 mgKOH/g or more, and further more preferably 150 mgKOH/g or more, from a viewpoint of improving the biodegradation rate of the resin molded body. The hydroxyl value of the cardanol compound is measured by a method A of ISO14900.

In a case where a cardanol compound having an epoxy group is used as the cardanol compound, the epoxy equivalent thereof is, for example, preferably 300 or more and 500 or less, more preferably 350 or more and 480 or less, and further more preferably 400 or more and 470 or less, from a viewpoint of improving the transparency of the resin molded body. The epoxy equivalent of the cardanol compound having an epoxy group is measured in accordance with ISO3001.

A molecular weight of the cardanol compound is, for example, preferably 250 or more and 1,000 or less, more preferably 280 or more and 800 or less, and further more preferably 300 or more and 500 or less, from a viewpoint of improving the biodegradation rate of the resin molded body.

One cardanol compound may be used alone, or two or more thereof may be used in combination.

A content of the plasticizer is, for example, preferably 1% by mass or more and 50% by mass or less, and more preferably 1% by mass or more and 30% by mass or less with respect to the entire biodegradable resin.

Other Components

The mother particles may contain other components.

Examples of the other components include a plasticizer, a flame retardant, a compatibilizer, a mold release agent, a light fastener, a weather resistant agent, a colorant, a pigment, a modifier, a drip inhibitor, an antistatic agent, a hydrolysis inhibitor, a filler, a reinforcing agent (glass fiber, carbon fiber, talc, clay, mica, glass flake, milled glass, glass beads, crystalline silica, alumina, silicon nitride, aluminum nitride, boron nitride, and the like), an acid acceptor to prevent acetic acid release (oxides such as magnesium oxide and aluminum oxide; metal hydroxides such as magnesium hydroxide, calcium hydroxide, aluminum hydroxide, and hydrotalcite; calcium carbonate; talc; and the like), a reactive trapping agent (for example, epoxy compound, acid anhydride compound, carbodiimides, and the like), and the like.

A content of the other components is, for example, preferably 0% by mass or more and 5% by mass or less, with respect to the total amount of the mother particles. Here, "0% by mass" means that other components are not contained.

The mother particles may contain resins other than the biodegradable resin. However, in a case of containing other resins, a content of other resins with respect to the total amount of the mother particles, for example, may be 5% by mass or less, and is preferably less than 1% by mass. Other resins are, for example, more preferably not contained (that is, 0% by mass).

Examples of other resins include known thermoplastic resins in the related art, specifically include a polycarbonate resin; a polypropylene resin; a polyester resin; a polyolefin resin; a polyester carbonate resin; a polyphenylene ether resin; a polyphenylene sulfide resin; a polysulfone resin; a polyether sulfone resin; a polyarylene resin; a polyetherimide resin; a polyacetal resin; a polyvinyl acetal resin; a polyketone resin; a polyether ketone resin; a polyetherether ketone resin; a polyaryl ketone resin; a polyether nitrile resin; a liquid crystal resin; a polybenzimidazole resin; a polyparavanate resin; a vinyl polymer or copolymer obtained by polymerizing or copolymerizing one or more vinyl monomers selected from the group consisting of aromatic alkenyl compound, methacrylic acid ester, acrylic acid ester, and vinyl cyanide compound; diene-aromatic alkenyl compound copolymer; vinyl cyanide-diene-aromatic alkenyl compound copolymer; aromatic alkenyl compound-diene-vinyl cyanide-N-phenylmaleimide copolymer; vinyl cyanide-(ethylene-diene-propylene (EPDM))-aromatic alkenyl compound copolymer; vinyl chloride resin; chlorinated vinyl chloride resin; and the like. One of these resins may be used alone, or two or more thereof may be used in combination.

Coating Layer

The resin particles include a coating layer containing at least one selected from the group consisting of a quaternary ammonium salt-containing polymer, polyacrylamide, polyvinylpyrrolidone, and polylysine on a surface of the mother particles.

A weight average molecular weight of the quaternary ammonium salt-containing polymer, polyacrylamide, polyvinylpyrrolidone, and polylysine is, for example, preferably 4,000 or more, more preferably 40,000 or more, further more preferably 100,000 or more, further more preferably 200,000 or more, preferably 3 million or less, more preferably 2 million or less, and further more preferably 1 million or less.

Here, the weight average molecular weights of the quaternary ammonium salt-containing polymer, polyacrylamide, polyvinylpyrrolidone, and polylysine are values measured by gel permeation chromatography (GPC).

The measurement is performed with a THF solvent, using GPC/HLC-8120GPC manufactured by Tosoh Corporation as a measuring apparatus, and using Column/TSKgel SuperHM-M (15 cm) manufactured by Tosoh Corporation. The weight average molecular weight is calculated from this measurement result using a molecular weight calibration curve prepared from a monodisperse polystyrene standard sample.

A surface coating amount of the coating layer is, for example, preferably 0.01% by mass or more and 20% by mass or less, more preferably 0.1% by mass or more and 10% by mass or less, and further more preferably 0.3% by mass or more and 5% by mass or less, with respect to the mother particles.

By setting the surface coating amount of the coating layer within the above range, the slipperiness of the resin particle surface is easily improved, and the fluidity of the resin particles is further improved.

Here, the surface coating amount of the coating layer is measured as follows. The coating amount of the cationic resin is obtained from a difference between a treated amount of at least one (hereinafter, also referred to as surface-treated polymer) selected from the group consisting of the quaternary ammonium salt-containing polymer, polyacrylamide, polyvinylpyrrolidone, and polylysine and a surface-treated polymer obtained by drying a supernatant after treatment.

Quaternary Ammonium Salt-Containing Polymer

The quaternary ammonium salt-containing polymer refers to a polymer having a structural unit containing an atomic group represented by $NR_4^+$ (R each indicates the same or different hydrocarbon groups).

Examples of the quaternary ammonium salt-containing polymer include a homopolymer of dimethyldiallylammonium chloride, a copolymer of dimethyldiallylammonium chloride and a (meth)acrylic group-containing monomer, a homopolymer of 2-methacryloyloxyethyl phosphorylcholine, a copolymer of 2-methacryloyloxyethyl phosphorylcholine and (meth)acrylic group-containing monomer, and the like.

Examples of the (meth)acrylic group-containing monomer include (meth)acrylic acid ester, (meth)acrylamide, and (meth)acrylic acid, and the like.

The (meth)acrylic acid ester is, for example, preferably (meth)acrylic acid alkyl ester, preferably (meth)acrylic acid alkyl ester in which the number of carbon atoms of the (meth)alkyl group is 2 or more and 25 or less, more preferably (meth)acrylic acid alkyl ester in which the number of carbon atoms of the alkyl group is 4 or more and 20 or less, and further more preferably (meth)acrylic acid alkyl ester in which the number of carbon atoms of the alkyl group is 10 or more and 19 or less.

Specific examples of the (meth)acrylic acid ester include methyl(meth)acrylate, ethyl(meth)acrylate, propyl(meth)acrylate, isopropyl(meth)acrylate, and n-butyl(meth)acrylate, isobutyl(meth)methacrylate, n-hexyl(meth)acrylate, 2-ethylhexyl(meth)acrylate, lauryl(meth)acrylate, stearyl(meth)acrylate, cyclohexyl(meth)acrylate, dicyclopentanyl (meth)acrylate, isobornyl(meth)acrylate, and the like.

One (meth)acrylic acid ester may be used alone, or two or more thereof may be used in combination.

A mass ratio of (meth)acrylic group-containing monomer in total polymerization components of the copolymer of dimethyldiallylammonium chloride and (meth)acrylic group-containing monomer and the copolymer of 2-methacryloyloxyethyl phosphorylcholine and (meth)acrylic group-containing monomer is, for example, preferably 10% by mass or more and 60% by mass or less, more preferably 15% by mass or more and 50% by mass or less, and further more preferably 20% by mass or more and 40% by mass or less.

A weight average molecular weight of the quaternary ammonium salt-containing polymer is, for example, preferably 50,000 or more, more preferably 100,000 or more, further more preferably 200,000 or more, further more preferably 300,000 or more, preferably 3 million or less, more preferably 2 million or less, and further more preferably 1 million or less.

Here, the weight average molecular weight of the quaternary ammonium salt-containing polymer is a value measured by gel permeation chromatography (GPC).

The quaternary ammonium salt-containing polymer is, for example, preferably at least one selected from the group consisting of polyquaternium-6, polyquaternium-7, polyquaternium-51, polyquaternium-61, and polyquaternium-64.

By using the compound as the quaternary ammonium salt-containing polymer, the slipperiness of the resin particle surface is easily further improved, and the fluidity of the resin particles is further improved.

Second Layer

A compound layer may be provided on the coating layer (hereinafter, also referred to as the first layer). Hereinafter, in a case where a compound layer is provided on the coating layer, the compound layer is referred to as a second layer.

The second layer, for example, is not limited and preferably contains an anionic or nonionic compound or a hydrophobic compound.

Examples of the anionic or nonionic compound or the hydrophobic compound include a hydrophobic compound having an anionic group (—COOH (carboxyl group), —SO3H (sulfone group), and the like), a hydrophobic compound not having a cationic group and an anionic group, and the like.

The hydrophobic compound indicates a compound that imparts hydrophobicity (specifically, a water contact angle) to the biodegradable resin particles described later.

Examples of the hydrophobic compound include silicone compound, hydrocarbon compound, fatty acid compound, acrylic resin, polyester resin, urethane resin, and the like.

Among these, at least one selected from the group consisting of silicone compound, hydrocarbon compound, fatty acid compound, acrylic resin, polyester resin, and urethane resins is, for example, preferable.

Examples of the silicone compound include dimethylpolysiloxane, methylpolysiloxane, octamethylcyclotetrasiloxane, decamethylcyclopentanesiloxane, methylcyclopolysiloxane, and various modified silicone oils (alkyl-modified silicone oil, polyether-modified silicone oil, alcohol-modified silicone oil, fluorine-modified silicone oil, amino-modified silicone oil, and the like), MQ resin, silicone rubber, and the like.

Among these, the silicone compound is, for example, preferably at least one selected from the group consisting of dimethylpolysiloxane, methylpolysiloxane, MQ resin, and silicone rubber.

Here, the MQ resin indicates a silicone resin having an M unit that is a monofunctional siloxane unit [(CH3)3SiO1/2] and a Q unit that is a tetrafunctional siloxane unit [SiO4/2].

Examples of the commercially available silicone compound include a silicone compound (KM-902, KM-903, KM-910, KM-9729, POLON-MN-ST, KM-9737A, KM-9782, KM-9738A, KM-752T, POLON-MF-33, KM-9717, X-51-1302M (MQ resin), POLON-MF-56, KM-2002-L-1, KM-2002-T, KM-9772, KM-9749, POLON-MF-40, KM-9729, X-52-1133, and the like, manufactured by Shin-Etsu Chemical Co., Ltd.), a silicone compound (BESIL DM3112VP) manufactured by Wacker Asahikasei Silicone Co., Ltd., and the like.

Examples of the hydrocarbon compound include petroleum wax (paraffin wax, microcrystalline wax, petrolatum wax, and the like), synthetic hydrocarbon wax (polyethylene wax, polypropylene wax, polybutene wax, Fischer Tropsch wax, and the like), and the like.

Among these, the hydrocarbon compound is, for example, preferably at least one selected from the group consisting of paraffin wax, microcrystalline wax, polyethylene wax, and polypropylene wax.

Examples of the commercially available hydrocarbon compound include microcrystalline wax (EMUSTAR-0001 and the like) manufactured by Nippon Seiro Co., Ltd., paraffin wax (EMUSTAR-0135 and the like) manufactured by Nippon Seiro Co., Ltd., paraffin wax (AQUACER497 and the like) manufactured by BYK Co., Ltd., polyethylene wax (AQUACER507, AQUACER840, AQUACER1547, AQUACER272, and the like) manufactured by BYK Co., Ltd., polyethylene wax (Hitech E-2213, Hitech E-6324, and the like) manufactured by Toho Chemical Industry Co., Ltd., polypropylene wax (AQUACER593 and the like) manufactured by BYK Co., ltd., polypropylene (Hitech P-9018, Hitech P-5060P, and the like) manufactured by Toho Chemical Industry Co., Ltd., and the like.

Examples of the fatty acid compound include vegetable oils containing fatty acids (castor oil, tung oil, flaxseed oil, shortening, corn oil, soybean oil, sesame oil, rapeseed oil, sunflower oil, rice bran oil, camellia oil, coconut oil, palm oil, walnut oil, olive oil, peanut oil, almond oil, jojoba oil, cacao butter, shea butter, neem oil, safflower oil, wood wax, candelilla wax, rice wax, carnauba wax, and the like) and the like.

Among these, from a viewpoint of improving the biodegradation rate over time and decreasing the initial biodegradation rate, the fatty acid compound is, for example, preferably at least one selected from the group consisting of carnauba wax, rice wax, candelilla wax, palm wax, castor oil wax, soybean oil wax, sunflower oil wax, and the like.

Examples of the commercially available fatty acid compound include carnauba wax (EMUSTAR-0413) (carnauba wax) manufactured by Nippon Seiro Co., Ltd., rice wax (AQUASPROUT-7300 and the like) manufactured by Nippon Seiro Co., Ltd., palm wax (AQUASPROUT-7100 and the like) manufactured by Nippon Seiro Co., Ltd., castor oil wax (AQUASPROUT-7500 and the like) manufactured by Nippon Seiro Co., Ltd., soybean oil wax (AQUASPROUT-7200 and the like) manufactured by Nippon Seiro Co., Ltd., sunflower oil wax (AQUASPROUT-7400 and the like) manufactured by Nippon Seiro Co., Ltd., palm oil wax (Kakko Ace TKE and the like) manufactured by Nippon Seiro Co., Ltd., and the like.

Examples of the acrylic resin include known acrylic resins such as a polymer of acrylic acid and a polymer of an acrylic acid alkyl ester.

Examples of the commercially available acrylic resin include acrylic resins (3WX-2015, 3MF-320, 3MF-333, 3MF-407, and the like) manufactured by Taisei Fine Chemical Co., Ltd., acrylic resins (Coat SFC-6440, Boncoat CE-6270, Boncoat CE-6400, Boncoat CF-2800, and the like) manufactured by DIC Corporation, and the like.

Examples of the polyester resin include known polyester resins such as a polycondensate of a polyvalent carboxylic acid and a polyhydric alcohol, a ring-opened polycondensate of cyclic lactam, and the like.

Examples of the commercially available polyester resin include polyester resins (A-110F, A-160P, A-520, A-613D, A-615GE, A-640, A-645GH, A-647GEX, and the like) manufactured by Takamatsu Oil & Fat Co., Ltd., and the like.

Examples of the urethane resin include known urethane resins such as polyester-based polyurethane, polyether-based polyurethane, polycarbonate-based polyurethane, and the like. In addition, as the urethane resin, a material having a urethane polymer shell layer around the core of the acrylic polymer may be used.

Examples of the commercially available urethane resin include urethane resins (WEM-031U, WEM-200U, WEM-321U, WEM-3000, WBR-016U, WBR-2101, and the like) manufactured by Taisei Fine Chemical Co., Ltd. and the like.

Content of Each Layer

In the biodegradable resin particles according to the present exemplary embodiment, a mass ratio of a coating amount of the cationic resin in the first layer to a coating amount of the hydrophobic compound in the second layer (coating amount of cationic resin/coating amount of hydrophobic compound) is, for example, preferably 0.05 or more and 20 or less, more preferably 0.1 or more and 10 or less, and further more preferably 0.1 or more and 3 or less.

In addition, a content of the cationic resin with respect to the mother particles (coating amount of the first layer with respect to the total amount of the mother particles) is, for example, preferably 0.05% by mass or more and 15% by mass or less, more preferably 0.1% by mass or more and 10% by mass or less, and further more preferably 0.1% by mass or more and 3% by mass or less.

In addition, from a viewpoint of further improving the storage properties in a solution containing water, a content of the hydrophobic compound with respect to the mother particles (coating amount of the second layer with respect to the total amount of the mother particles) is, for example, preferably 0.05% by mass or more and 15% by mass or less, more preferably 0.1% by mass or more and 10% by mass or less, and further more preferably 0.1% by mass or more and 3% by mass or less.

Here, the coating amount of the second layer is measured as follows. The coating amount of the hydrophobic compound is obtained from a difference between a treated amount of the hydrophobic compound and the hydrophobic compound obtained by drying a supernatant after the treatment.

Dynamic Friction Coefficient

The resin particles according to the present exemplary embodiment have a dynamic friction coefficient of 0.5 or less.

From a viewpoint of further improving the fluidity of the resin particles, the dynamic friction coefficient is, for example, preferably 0.5 or less, more preferably 0.4 or less, and further more preferably 0.3 or less.

From a viewpoint of improving the fluidity of the resin particles, the smaller the dynamic friction coefficient is, the more preferable the resin particles are, for example. For example, the dynamic friction coefficient may be 0.01 or more, may be 0.05 or more, or may be 0.1 or more.

The dynamic friction coefficient is measured by the following procedure.

An artificial skin (Bioskin, manufactured by Beaulax Co., Ltd.) coated with particles to be measured so as to be 0.5 $mg/cm^2$ is used as a measurement sample, and is measured using a friction tester (HEIDON), using as a contactor a pseudo-fingertip sensor (10 mm square piano wire sensor, manufactured by Kato Tech Co., Ltd.), an overload of 25 g, a speed of 1 mm/sec, and a test distance of 20 mm.

Particle Size

A volume average particle size of the resin particles is, for example, preferably 3 μm or more and 100 μm or less, more preferably 5 μm or more and 70 μm or less, and further more preferably 8 μm or more and 60 μm or less.

A large-diameter side number particle size distribution index GSDv of the biodegradable resin particles is, for example, preferably 1.5 or less, more preferably 1.3 or less, and further more preferably 1.2 or less.

The volume average particle size and the large diameter side particle size distribution index GSDp of the biodegradable resin particles are measured as follows.

A particle size is measured by an LS particle size distribution measuring apparatus "Beckman Coulter LS13 320 (manufactured by Beckman Coulter)", the cumulative distribution of the particle size is drawn from the small diameter side on a volume basis, and the particle size that becomes 50% of accumulation is obtained as the volume average particle size.

On the other hand, the cumulative distribution of particle size is drawn from the small diameter side on a volume basis, and the particle size that becomes 50% of accumulation is defined as a number average particle diameter $D50v$, and the particle size that becomes 84% of accumulation is defined as a number particle size $D84v$. Then, the large-diameter side number particle size distribution index GSDv is calculated by Formula $GSDv=(D84v/D50v)^{1/2}$.

Method for Producing Resin Particles

Examples of a method for producing resin particles include the following methods.

First Step

In First step, mother particles are prepared.

Examples of the method for producing the mother particles include the following methods (1) to (5).

(1) A kneading and pulverizing method of obtaining granules by kneading each component, and pulverizing and classifying obtained kneaded matters (2) A dry production method of obtaining granules by changing a shape of the granules obtained by the kneading and pulverizing method with a mechanical impact force or thermal energy (3) An aggregation and coalescence method of obtaining granules by mixing a particle dispersion solution of each component, and aggregating and heat-fusing particles in the dispersion solution (4) A dissolution suspension method of granulating granules including each component by suspending an organic solvent in which each component is dissolved in an aqueous solvent (5) A kneading and dissolution method of granulating by kneading each component and a binder, extruding thereof into pellets, and agitating the obtained pellets in a solvent dissolving only the binder Subsequently, an aqueous dispersion solution in which the obtained mother particles are dispersed is prepared. Before preparing the aqueous dispersion solution, acid washing of the mother particles may be, for example, performed.

Subsequently, the aqueous dispersion solution and an aqueous solution containing the aqueous dispersion solution in which the mother particles are dispersed and a surface-treated polymer are mixed with each other. With this, for example, a hydroxyl group of the resin contained in the mother particles reacts with an amine site of the surface-treated polymer to form a coating layer. Then, the resin particles on which the coating layer is formed are extracted from the mixed solution. The extraction of the resin particles on which the coating layer is formed is, for example, performed by filtering the mixed solution. The extracted resin particles on which the coating layer is formed may be, for example, washed with water. With this, the unreacted surface-treated polymer is removed. Then, the resin particles on which the coating layer is formed are dried to obtain the resin particles according to the present exemplary embodiment.

Use

Examples of the use of the resin particles according to the present exemplary embodiment include cosmetics, rolling materials, abrasives, scrubbing agents, display spacers, beads molding materials, light diffusing particles, resin strengthening agents, refractive index control agents, biodegradation accelerators, fertilizers, water-absorbent particles, toner particles, granules of anti-blocking particles, and the like.

The use of the resin particles according to the present exemplary embodiment is, for example, preferably cosmetics.

Among these, the use of the resin particles according to the present exemplary embodiment is, for example, preferably a cosmetic base material.

Since the resin particles according to the present exemplary embodiment have excellent fluidity, in a case of being used as a cosmetic base material, in a case where the cosmetic is applied on the skin, the spread of the cosmetic on the skin easily becomes good.

In addition, since the resin particles according to the present exemplary embodiment have a low friction coefficient, in a case of being used as a cosmetic base material, the portion to which the cosmetics are applied easily has a good feel.

Specific examples of the cosmetic base material include cosmetic base materials such as base makeup cosmetics (for example, makeup base, concealer, foundation, face powder, and the like); makeup cosmetics (for example, lipstick, gloss, lip liner, blush, eye shadow, eyeliner, mascara, eyebrow, nails, nail care cosmetics, and the like); and skin care cosmetics (for example, facial wash material, cleansing, lotion, emulsion, liquid cosmetics, pack, face mask, eye and mouth care cosmetics, and the like).

In particular, for the cosmetic base material of makeup cosmetics, the resin particles according to the present exemplary embodiment are, for example, preferably used as a cosmetic base material of makeup cosmetics, from a viewpoint that the cosmetic base material of makeup cosmetics is required to have flexibility, heat resistance, and biodegradability.

Here, the cosmetic base material means a component to maintain a formulation of a cosmetic composition.

EXAMPLES

Examples will be described below, but the present invention is not limited to these examples. In the following description, unless otherwise specified, "parts" and "%" are all based on mass.

Preparation of Each Material

The following materials are prepared.

Biodegradable Resin of Mother Particles

CAP: Cellulose acetate propionate, weight average polymerization degree 716, acetyl group substitution degree 0.18, propionyl group substitution degree 2.49

CAB: Eastman Chemical "CAP504-0.2", cellulose acetate propionate, weight average polymerization degree 133, acetyl group substitution degree 0.04, propionyl group substitution degree 2.09

PLA: Polylactic acid (weight average molecular weight 180,000)
PBS: Polybutylene succinate (weight average molecular weight 200,000)
PA12: Polyamide 12
DAC: "L-50" manufactured by Daicel Corporation, cellulose diacetate, weight average polymerization degree 570
CAP2: Cellulose acetate phthalate Plasticizer for Mother Particles
  CDN1: "NX-2503" manufactured by Cardolite Corporation, hydroxyethylated cardanol, molecular weight 296 to 320
  CDN2: "Ultra LITE 513" manufactured by Cardolite Corporation, glycidyl ether of cardanol, molecular weight 354 to 361
  CDN3: "EPICLON865-alkyl-modified product" manufactured by DIC, alkyl-modified product of phenol novolac type epoxy resin
  DBA: Diisobutyl adipate
  ATBC: Tributyl 0-acetyl citrate
  TEH: Triethylhexanoin Polymer of Coating Layer
  Cosmote VH: Polyoctanium-7 manufactured by Senka Co., Ltd.
  Cosmote VGN: Polyoctanium-6 manufactured by Senka Co., Ltd.
  Lipidure-S: Polyoctanium-61 manufactured by NOF Corporation
  Polyacrylamide: Weight average molecular weight 400,000
  Polyvinylpyrrolidone: Weight average molecular weight 40,000
  Polylysine: Weight average molecular weight 5,000
  Epomin P-1000: Polyethyleneimine manufactured by Nippon Shokubai Co., Ltd.
  LIPIDURE-PMB: Polyoctanium-51 manufactured by NOF Corporation
  LIPIDURE-C: Polyoctanium-64 manufactured by NOF Corporation
  K-434: Cationic polyvinyl alcohol manufactured by Mitsubishi Chemical Corporation (referred to as "cationized polyvinyl alcohol" in the table)

Examples 1 to 31, Comparative Example 2

Preparation of Resin Pellets

A cylinder temperature is adjusted at a charged composition ratio shown in Table 1, and kneading is performed with a twin-screw kneader (TEX41SS manufactured by Toshiba Machine Co., Ltd.) to obtain a pellet-shaped resin composition (hereinafter, referred to as resin pellet).

Preparation of Mother Particles 300 g of resin pellets are completely dissolved in 700 g of methyl ethyl ketone. This is added to an aqueous liquid in which 100 g of calcium carbonate, 4 g of carboxymethyl cellulose, and 200 g of methyl ethyl ketone are dispersed in 1,100 g of pure water, and the mixture is agitated for 3 hours. This is added with 10 g of sodium hydroxide, and the mixture is heated to 80° C. and agitated for 3 hours to remove methyl ethyl ketone (hereinafter, this is referred to as removal of methyl ethyl ketone "solvent removal"). After filtering the residue, the resultant product is dispersed in pure water again to obtain a slurry of mother particles.

On the other hand, in a case where a resin other than DAC, CAB, and CAP is used as the resin, mother particles are obtained as follows.

2,000 g of resin pellets are melt-kneaded (kneader), the kneaded product is rolled with two rolls to form a plate, and then the molded product is cooled and coarsely pulverized by a pulverizer. The coarsely pulverized product is finely pulverized with a jet mill to obtain mother particles. The mother particles are dispersed in pure water to obtain a slurry of mother particles.

Preparation of Coating Layer

Using the polymer of the coating layer shown in Table 1, resin particles are obtained as follows so that the coating amount is the amount shown in Table 1.

After adjusting the slurry of the mother particles so that the solid content is 20%, a predetermined amount of a solution of the polymer of the coating layer is added to the solid content contained in the slurry in terms of pure content under a condition of 25° C., and agitated for 1 hour. After the agitating is completed, the residue is filtered, washed with pure water, and the solid content is freeze-dried to obtain resin particles.

Through the above steps, resin particles are obtained.

Comparative Example 1

In the preparation of the mother particles, resin particles are obtained in the same procedure as in Example 1 except that after removing the solvent, the residue is filtered, and the obtained mother particles are freeze-dried (that is, the coating layer is not prepared).

Evaluation

For the obtained resin particles, the number average particle diameter D50v and the dynamic friction coefficient are measured according to the described method.

Then, the fluidity of the resin particles is evaluated according to the following evaluation criteria using the value of the dynamic friction coefficient.

(Fluidity Evaluation Criteria)
  A: Dynamic friction coefficient is less than 0.3
  B: Dynamic friction coefficient is 0.3 or more and less than 0.4
  C: Dynamic friction coefficient is 0.4 or more and less than 0.5
  D: Dynamic friction coefficient is 0.5 or more

TABLE 1

| | Resin | | Plasticizer | | Polymer of coating layer | Coating amount (%, to mother particles) | D50v (μm) | Friction coefficient | Fluidity evaluation |
|---|---|---|---|---|---|---|---|---|---|
| | Type | Parts | Type | Parts | Type | | | | |
| Example 1 | CAP | 100 | CDN1 | 20 | Polyoctanium-7 | 0.5 | 7 | 0.27 | A |
| Example 2 | CAP | 100 | CDN1 | 20 | Polyoctanium-7 | 0.1 | 7 | 0.35 | B |
| Example 3 | CAP | 100 | CDN1 | 20 | Polyoctanium-7 | 10 | 7 | 0.32 | B |
| Example 4 | CAP | 100 | CDN1 | 20 | Polyoctanium-6 | 0.5 | 7 | 0.33 | B |
| Example 5 | CAP | 100 | CDN1 | 20 | Polyoctanium-51 | 0.5 | 7 | 0.30 | B |

TABLE 1-continued

| | Resin | | Plasticizer | | Polymer of coating layer | Coating amount (%, to mother particles) | D50v (μm) | Friction coefficient | Fluidity evaluation |
|---|---|---|---|---|---|---|---|---|---|
| | Type | Parts | Type | Parts | Type | | | | |
| Example 6 | CAP | 100 | CDN1 | 20 | Polyoctanium-61 | 0.5 | 7 | 0.31 | B |
| Example 7 | CAP | 100 | CDN1 | 20 | Polyoctanium-64 | 0.5 | 7 | 0.34 | B |
| Example 8 | CAP | 100 | CDN1 | 20 | Polyacrylamide | 0.5 | 7 | 0.32 | B |
| Example 9 | CAP | 100 | CDN1 | 20 | Polyvinylpyrrolidone | 0.5 | 7 | 0.35 | B |
| Example 10 | CAP | 100 | CDN1 | 20 | Polylysine | 0.5 | 7 | 0.36 | B |
| Example 11 | CAB | 100 | CDN1 | 20 | Polyoctanium-7 | 0.5 | 7 | 0.35 | B |
| Example 12 | CAB | 100 | DBA | 20 | Polyoctanium-7 | 0.5 | 7 | 0.37 | B |
| Example 13 | CAB | 100 | ATBC | 20 | Polyoctanium-7 | 0.5 | 7 | 0.38 | B |
| Example 14 | CAB | 100 | DPS | 20 | Polyoctanium-7 | 0.5 | 7 | 0.36 | B |
| Example 15 | CAP | 100 | DBA | 20 | Polyoctanium-7 | 0.5 | 7 | 0.38 | B |
| Example 16 | CAP | 100 | CDN2 | 20 | Polyoctanium-7 | 0.5 | 7 | 0.39 | B |
| Example 17 | CAP | 100 | CDN3 | 20 | Polyoctanium-7 | 0.5 | 7 | 0.36 | B |
| Example 18 | CAP | 100 | — | — | Polyoctanium-7 | 0.5 | 7 | 0.40 | C |
| Comparative Example 1 | CAP | 100 | CDN1 | 20 | — | — | 7 | 0.54 | D |
| Comparative Example 2 | CAP | 100 | CDN1 | 20 | Polyethyleneimine | 0.5 | 7 | 0.56 | D |
| Example 19 | CAP | 100 | CDN1 | 20 | Cationized polyvinyl alcohol | 0.5 | 7 | 0.45 | C |
| Example 20 | PLA | 100 | — | — | Polyoctanium-7 | 0.5 | 7 | 0.43 | C |
| Example 21 | PBS | 100 | — | — | Polyoctanium-7 | 0.5 | 7 | 0.47 | C |
| Example 22 | PA12 | 100 | — | — | Polyoctanium-7 | 0.5 | 7 | 0.45 | C |
| Example 23 | DAC | 100 | — | — | Polyoctanium-7 | 0.5 | 7 | 0.38 | B |
| Example 24 | CAP2 | 100 | — | — | Polyoctanium-7 | 0.5 | 7 | 0.48 | C |
| Example 25 | CAP | 100 | TEH | 20 | Polyoctanium-7 | 0.5 | 7 | 0.48 | C |
| Example 26 | CAP | 100 | CDN1 | 20 | Polyoctanium-7 | 0.008 | 7 | 0.49 | C |
| Example 27 | CAP | 100 | CDN1 | 20 | Polyoctanium-7 | 0.02 | 7 | 0.39 | B |
| Example 28 | CAP | 100 | CDN1 | 20 | Polyoctanium-7 | 19 | 7 | 0.38 | B |
| Example 29 | CAP | 100 | CDN1 | 20 | Polyoctanium-7 | 23 | 7 | 0.41 | C |
| Example 30 | CAP | 100 | CDN1 | 5 | Polyoctanium-7 | 0.5 | 7 | 0.48 | C |
| Example 31 | CAP | 100 | CDN1 | 40 | Polyoctanium-7 | 0.5 | 7 | 0.47 | C |

From the above results, it is recognized that the resin particles of the present example have high fluidity.

Since the resin particles of the present example have high fluidity and low friction coefficient, it is recognized that the resin particles are appropriate as a cosmetic base material.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. Resin particles comprising:
   mother particles containing a biodegradable resin; and
   a coating layer containing at least one selected from the group consisting of a quaternary ammonium salt-containing polymer and polyacrylamide on a surface of the mother particles,
   wherein the biodegradable resin comprises cellulose acylate, wherein a substitution degree of cellulose acylate is 2.1 or more and 2.9 or less,
   wherein the cellulose acylate is at least one selected from the group consisting of cellulose acetate and cellulose acetate propionate,
   wherein the mother particles contain a plasticizer containing a functional group that reacts with a compound contained in the coating layer comprising an ester compound, a cardanol compound, a camphor, a metal soap, a polyol, or a polyalkylene oxide.

2. The resin particles according to claim 1,
   wherein the quaternary ammonium salt-containing polymer is at least one selected from the group consisting of polyquaternium-6, polyquaternium-7, polyquaternium-51, polyquaternium-61, and polyquaternium-64.

3. The resin particles according to claim 1,
   wherein the plasticizer is at least one of an ester compound or a cardanol compound.

4. The resin particles according to claim 1,
   wherein a surface coating amount of the coating layer is 0.01% by mass or more and 20% by mass or less with respect to the mother particles.

5. Resin particles according to claim 1 comprising:
   mother particles containing a biodegradable resin; and
   a coating layer on a surface of the mother particles,
   wherein the resin particles comprise a dynamic friction coefficient of 0.5 or less.

6. The resin particles according to claim 1, which are for cosmetic use.

* * * * *